(12) United States Patent
Barraza et al.

(10) Patent No.: US 9,795,759 B2
(45) Date of Patent: Oct. 24, 2017

(54) LOW FLOW CONTROLLER

(71) Applicant: CareFusion 2200, Inc., San Diego, CA (US)

(72) Inventors: Manuel Barraza, Huntington Beach, CA (US); Michael J. Cegielski, Norco, CA (US)

(73) Assignee: VYAIRE MEDICAL CONSUMABLES LLC, Yorba Linda, CA (US)

( * ) Notice: Subject to any disclaimer, the term of this patent is extended or adjusted under 35 U.S.C. 154(b) by 125 days.

(21) Appl. No.: 14/700,094

(22) Filed: Apr. 29, 2015

(65) Prior Publication Data

US 2016/0317779 A1 Nov. 3, 2016

(51) Int. Cl.
*F16K 15/03* (2006.01)
*A61M 16/20* (2006.01)
*F16K 7/12* (2006.01)
*F16K 25/00* (2006.01)

(52) U.S. Cl.
CPC ........ *A61M 16/206* (2014.02); *A61M 16/208* (2013.01); *F16K 7/12* (2013.01); *F16K 15/031* (2013.01); *F16K 25/005* (2013.01); *Y10T 137/7892* (2015.04)

(58) Field of Classification Search
CPC ........... Y10T 137/7771; Y10T 137/778; Y10T 137/7779; Y10T 137/7847; Y10T 137/7848; Y10T 137/7892; Y10T 137/7891; Y10T 137/7895; A62B 18/10; A62B 23/02; A61M 16/207
See application file for complete search history.

(56) References Cited

U.S. PATENT DOCUMENTS

| 1,480,608 | A | * | 1/1924 | Gardner | F01L 3/205 137/856 |
| 2,300,273 | A | * | 10/1942 | Connell | A62B 7/14 128/205.14 |
| 4,141,379 | A | * | 2/1979 | Manske | A61M 39/24 137/496 |
| 4,775,376 | A | | 10/1988 | Strung | |
| 4,982,842 | A | | 1/1991 | Hollister | |
| 5,125,415 | A | | 6/1992 | Bell | |
| 5,147,309 | A | | 9/1992 | Hemmerich et al. | |

(Continued)

FOREIGN PATENT DOCUMENTS

| CN | 203915716 U | 11/2014 |
| WO | WO-2007068341 A1 | 6/2007 |
| WO | WO-2015022629 A1 | 2/2015 |

OTHER PUBLICATIONS

International Search Report and Written Opinion for Application No. PCT/US2016/027141, dated Jul. 5, 2016, 12 pages.

*Primary Examiner* — Matthew W Jellett
(74) *Attorney, Agent, or Firm* — McDermott Will & Emery LLP (57) ABSTRACT

A flow controller can include a conduit wall and a membrane coupled to the conduit wall. The membrane is configured to obstruct gas flow through the conduit. The flow controller includes a membrane controller, positioned adjacent to the membrane, wherein the membrane is positioned on one side of the membrane controller, such that the membrane controller impedes bending of the membrane in a second direction different from the first direction, thereby restricting gas flow through the conduit.

20 Claims, 4 Drawing Sheets

(56) References Cited

U.S. PATENT DOCUMENTS

| | | | | |
|---|---|---|---|---|
| 5,261,448 A * | 11/1993 | Furuya | ................... | B60G 17/08 |
| | | | | 137/513.5 |
| 5,295,478 A * | 3/1994 | Baldwin | ........... | A61M 16/0048 |
| | | | | 128/202.28 |
| 5,342,320 A | 8/1994 | Cameron | | |
| 5,406,976 A * | 4/1995 | Bekki | ................ | F16H 61/0009 |
| | | | | 137/513.3 |
| 5,421,368 A * | 6/1995 | Maalouf | ................ | F04C 29/12 |
| | | | | 137/856 |
| 5,554,127 A | 9/1996 | Crouther et al. | | |
| 5,601,117 A * | 2/1997 | Lewis | ................... | B60H 1/249 |
| | | | | 137/527.8 |
| 5,647,395 A * | 7/1997 | Hashimoto | ......... | F04B 39/1073 |
| | | | | 137/514 |
| 5,881,722 A * | 3/1999 | DeVries | .............. | A61M 16/125 |
| | | | | 128/204.21 |
| 6,491,667 B1 | 12/2002 | Keane et al. | | |
| 6,877,511 B2 * | 4/2005 | DeVries | .............. | A61M 16/125 |
| | | | | 128/204.21 |
| 7,037,642 B2 | 5/2006 | Hei | | |
| 7,322,941 B2 | 1/2008 | Henshaw | | |
| 8,662,104 B2 * | 3/2014 | Hansmann | ........... | A61M 16/20 |
| | | | | 137/493 |
| 8,714,200 B2 * | 5/2014 | Bushman | ................ | A61C 1/16 |
| | | | | 137/843 |
| 9,278,186 B2 * | 3/2016 | Dantanarayana | .... | A61B 5/0876 |
| 2004/0149337 A1 | 8/2004 | Koeger et al. | | |
| 2009/0277206 A1 * | 11/2009 | Laufenberg | ............. | F16K 15/03 |
| | | | | 62/285 |
| 2013/0239971 A1 * | 9/2013 | Dantanarayana | .... | A61B 5/0876 |
| | | | | 128/205.24 |

* cited by examiner

LOW FLOW CONTROLLER

BACKGROUND

The subject technology generally relates to a low flow controller.

Bidirectional flow conduits allow gas to flow through the conduit in two directions. In some instances, it is desirable that the flows in the two directions at the same pressure. In other instances, it may be desirable that flows in the two directions have different pressures. For example, in a respiratory circuit, the flow conduit directly next to the patient's mouth or breathing orifice may provide bidirectional flows with different pressures in each direction. The inspiratory flow toward the patient from a ventilator may be provided at a greater pressure, in order to provide adequate air to and inflation of the lungs, than the expiratory flow from the patient, which may rely on the patient's own lung resiliency.

SUMMARY

Some aspects of the subject technology relate to a flow controller conduit that includes a flow controller within a flow conduit. The flow controller conduit includes a conduit wall. The flow controller conduit includes a membrane inside the conduit wall that obstructs gas flow within the flow controller conduit. The flow controller conduit includes a membrane controller adjacent to the membrane, wherein the membrane is positioned in a first direction from the membrane controller, and wherein the membrane controller impedes bending of the membrane, and thereby restricts or limits gas flow within the flow controller conduit, in a second direction different from the first direction.

Described herein are embodiments of a flow controller conduit comprising a conduit comprising a conduit wall: a membrane coupled to the conduit wall, the membrane obstructing gas flow through the conduit when the membrane is in a closed position; and a membrane controller coupled to the conduit wall adjacent the membrane, the membrane being positioned in a first direction from the membrane controller, and wherein the membrane controller impedes bending of the membrane, thereby restricting gas flow through the conduit and membrane, when the membrane bends in a second direction, different from the first direction. In some embodiments, the second direction is opposite the first direction, and the conduit wall extends in the first direction and the second direction.

In certain embodiments, the membrane, when in the closed position, resides within a plane perpendicular to the first direction and the second direction. Some embodiments provide that the membrane controller, when in a rest position, resides within a plane perpendicular to the first direction and the second direction. In some embodiments, the membrane controller comprises an elongate shape, extends diametrically across the conduit, and contacts the conduit wall at a first end of the elongate shape, but not at a second end of the elongate shape.

Some embodiments provide that the membrane controller comprises an elongate shape with a transverse portion that extends in a direction transverse to the elongate shape. In some embodiments, the membrane controller comprises an annular shape, and w herein the membrane controller contacts the conduit wall at only one segment of the annular shape. In some instances, the membrane comprises a circular shape that is coupled to the conduit wall at only one segment of the circular shape. In some embodiments, the membrane controller is spaced from the membrane and contacts the membrane only when the membrane bends toward the membrane controller.

In some instances, the membrane controller comprises a Mylar® (biaxially-oriented polyethylene terephthalate) material, and in some embodiments, the membrane comprises a Mylar® (biaxially-oriented polyethylene terephthalate) material and comprises a substantially equal thickness to the membrane controller. Some embodiments provide that the membrane controller comprises a thickness that is greater than a thickness of the membrane.

Some embodiments described a membrane controller comprising: an annular portion configured to contact a conduit wall, such that the membrane controller is configured to be secured within a conduit b the contact between the annular portion and the conduit wall; and an elongate portion extending across a central opening of the annular portion, the elongate portion being connected to the annular portion at only one end of the elongate portion; wherein the membrane controller is configured (i) to be positioned within the conduit on one side of a flexible membrane and (ii) to contact the flexible membrane with the elongate portion when the flexible membrane is deflected toward the membrane controller.

In some embodiments, the elongate portion is configured not to contact the flexible membrane when the flexible membrane is deflected away from the membrane controller. Some embodiments provide that the elongate portion comprises a Mylar® (biaxially-oriented polyethylene terephthalate) material. In some embodiments, the elongate portion comprises a transverse segment, spaced from the one end of the elongate portion, that extends transversely to a long axis of the elongate portion. In some instances, the elongate portion extends substantially diametrically across the central opening of the annular portion.

Described herein are methods of controlling flow through a conduit. Some methods include providing a membrane controller comprising: an annular portion secured within the conduit and positioned within the conduit on one side of a flexible membrane, such that the membrane controller contacts the flexible membrane with the elongate portion when the flexible membrane is deflected toward the membrane controller; an elongate portion extending across a central opening of the annular portion, the elongate portion being connected to the annular portion at only one end of the elongate portion; and conducting a fluid through the conduit (i) in a first direction, thereby causing the flexible membrane to deflect toward the membrane controller and (ii) in a second direction causing the flexible membrane to deflect away from the membrane controller. Some methods provide that the conducting a fluid through the conduit comprises connecting the conduit between a ventilator and a patient. In some methods, the membrane controller and the flexible membrane comprise Mylar® (biaxially-oriented polyethylene terephthalate) material.

The foregoing and other features, aspects and advantages of the disclosed embodiments will become more apparent from the following detailed description and accompanying drawings.

BRIEF DESCRIPTION OF THE DRAWINGS

Features of the subject technology are set forth in the appended claims. However, for purpose of explanation, several aspects of the disclosed subject matter are set forth in the following figures.

DETAILED DESCRIPTION OF THE PREFERRED EMBODIMENTS

Many bidirectional flow conduits allow gas to flow through the conduit at the same pressure in a first direction and in a second direction. However, such a uniform pressure bidirectional flow conduit may not be desirable in all situations. For example, when a patient is connected to a medical ventilator, during inhalation, the medical ventilator may move air into the lungs at a relatively high pressure. However, during exhalation, the patient may remove air from his/her lungs at a relatively low pressure. As the foregoing illustrates, a flow controller that allows gas to flow at a first pressure in a first direction and at a different, second pressure in a different, second direction may be desirable.

The subject technology provides, among other things, a flow controller that allows gas to flow at a first pressure in a first direction and at a different, second pressure in a different, second direction. In some implementations, a low flow controller that alters the gas flow in a bidirectional flow sensor is provided. The low flow controller may be a passive structure in a first direction. but in a different, second direction, the low flow controller may respond to changes in gas flow. The low flow controller may allow gas to flow in the second direction at a higher pressure differential than in the first direction due to a geometrical asymmetry of the low flow controller.

The subject technology is directed to a flow controller conduit. The flow controller conduit includes a conduit wall and a membrane coupled to the conduit wall such that the membrane may flex or bend at a coupling portion. The membrane obstructs gas flow within the flow controller conduit by impeding the flow while passing through the membrane, causing the membrane to flex or bend. The flow controller conduit includes a membrane controller adjacent to the membrane. The membrane is positioned in a first direction from the membrane controller or on one side of the membrane. The membrane controller impedes bending of the membrane, and thereby gas flow through the flow controller conduit, in a second direction different from the first direction. The second direction may be opposite to the first direction, and the conduit wall may extend in the first direction and the second direction.

The conduit wall may be a cylinder and may be made of metal or hard plastic. The membrane may be made of Mylar® (biaxially-oriented polyethylene terephthalate) or other materials, such as stainless steel, and the membrane controller may be made of Mylar® (biaxially-oriented polyethylene terephthalate). In some embodiments, other materials may include other composites and/or ferrous sheets.

The membrane may be circular and, when in a closed position, may reside within a plane substantially perpendicular to the first direction and the second direction. In the closed position, a circular edge of the membrane may substantially extend over the entire conduit pathway. The membrane controller, when in a resting position, or undeflected and unflexed, may reside within a line or a plane perpendicular to the first direction and the second direction.

The membrane controller may have an elongate shape, and may be coupled to the conduit wall at a first end of the elongate shape, but not at a second end of the elongate shape. Alternatively, the membrane controller may have a portion that extends transversely to a long axis of the elongate shape. For example, the membrane controller may have an uppercase "T" shape or a lowercase "t" shape. The membrane controller may engage the conduit wall at a bottom end of the uppercase "T" or the lowercase "t" shape (i.e., where the membrane controller is coupled to the conduit wall), but not at any other ends of the uppercase "T" shape or the lowercase "t" shape. In another embodiment, the membrane controller may have an annular or annular shape, where the outer diameter of the membrane controller is smaller than the inner diameter of the conduit wall. The membrane controller may engage the conduit wall at only one intersection point between the outside of the membrane controller and the inside of the conduit wall (i.e., where the membrane controller is coupled to the conduit wall).

The membrane may have an equal thickness as the membrane controller. Alternatively, the membrane may have a lesser thickness than the membrane controller. In another alternative, the membrane may have a greater thickness than the membrane controller. The degree to which the membrane is desired to impede flexing or bending of the membrane will determine the relative thickness between the membrane and the membrane controller. For example, if the membrane itself is intended to provide a significant portion of the resisting force, the membrane can have a greater thickness than the membrane controller, such that the membrane controller merely slightly impedes flexing or bending of the membrane. This arrangement may be desirable when the differential pressure between the first and second flow directions is not significant. In some embodiments, the membrane may be intended to provide only a minor portion of the resisting or impeding force. In such situations, the membrane may have a lesser thickness than the membrane controller, such that the membrane merely slightly impedes flexing or bending, and the membrane controller provides a greater portion of the resistance. This arrangement may be desirable when the differential pressure between the first and second flow directions is greater than the example provided above.

Figure 1A:
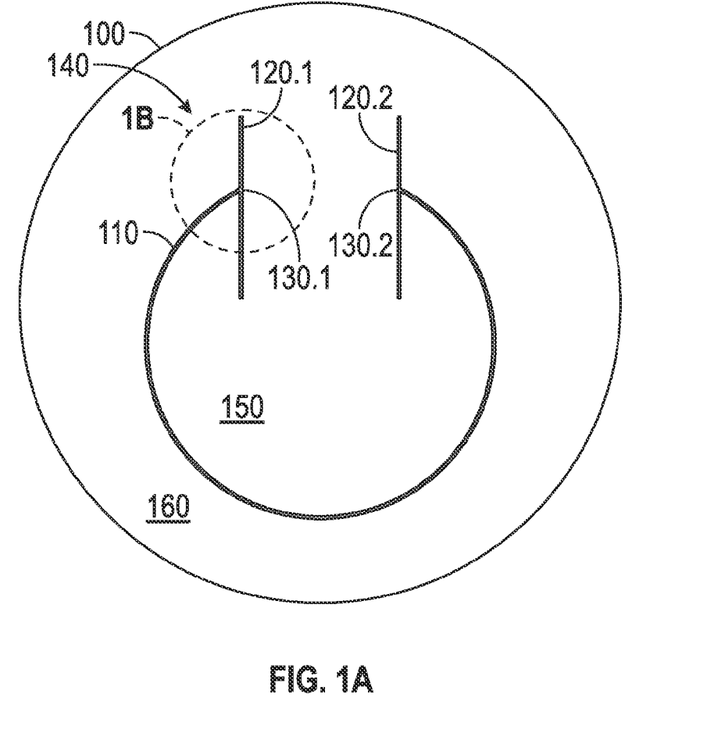
FIGS. 1A-1B rate examples of a flow membrane that impedes or restricts flow in a flow conduit.
Figure 1B:
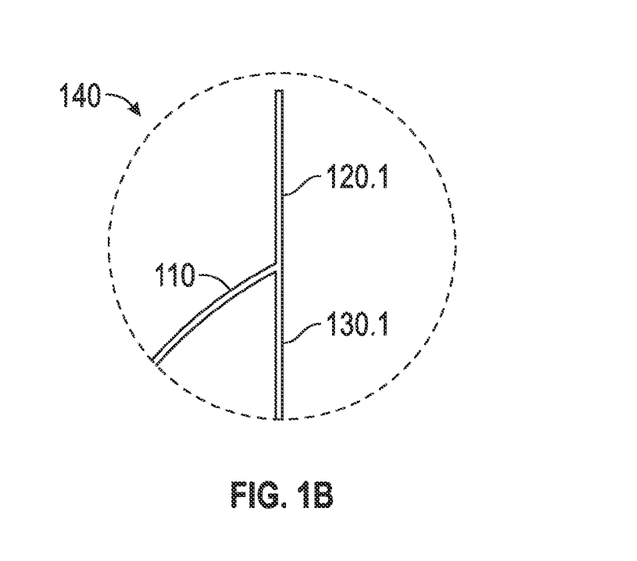

FIGS. 1A-1B illustrates examples of a sheet 100 used to construct a membrane 150. The sheet 100 may be flat or significantly flat (e.g., with deflections up to 0.001 inches per inch).

FIG. 1A illustrates the full sheet 100. The material of the sheet 100 may be Mylar® (biaxially-oriented polyethylene terephthalate), and the sheet 100 may be 0.003 inches thick or between 0.002 and 0.004 inches thick. Alternatively, the sheet 100 may have other thicknesses depending on the pressure differentials desired and the fluid conducted through the flow conduit. As shown, the sheet 100 may have a circular shape. A slit 110 having a shape of a portion of a circle may be cut within the sheet 100. Two parallel or roughly parallel (e.g., within 5, 10, 20, etc., degrees of parallel) slits 120.1 and 120.2 may be cut to intersect with the slit 110 at its endpoints 130.1 and 130.2, respectively.

FIG. 1B illustrates a zoomed-in view of a portion 140 of the sheet 100. FIG. 1B illustrates the intersection point 130.1 between slit 110 and slit 120.1. As show in FIG. 1B, the width of the slits 110, 120.1, and 120.2 may be 0.004+/−0.001 inches.

Returning to FIG. 1A, after the slits 110. 120.1, and 120.2 are cut, a circular membrane 150 may be bent out of the sheet 100, leaving an annular part 160 of the original sheet 100. The annular part 160 of the sheet 100 may be formed by laser cut or may be photo-etched, and the sheet may be connected or coupled to a conduit wall. For example, the annular part 160 may be coupled adjoining portions of the conduit wall by friction fit, welding, gluing, or by a similar manner. As further illustrated in FIG. 1A, the diameter of the membrane 150 may be 0.500+/−0.001 inches. In some embodiments, the diameter of the membrane 150 may be different, depending on the fluid flowing through the conduit or on the desired flow pressure differentials desired.

Figures 2A, 2B:
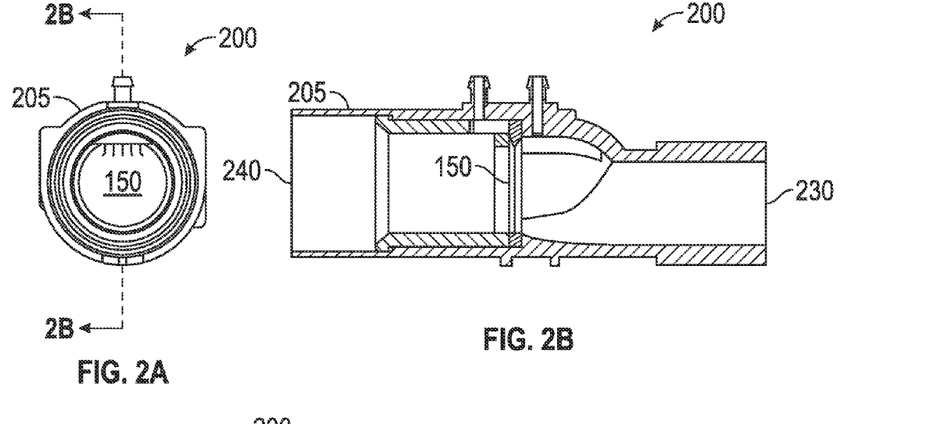
FIG. 2A-2D illustrate examples of a flow controller conduit.

FIGS. 2A-2D illustrate examples of a flow controller conduit 200. FIG. 2A provides an axial interior view of the conduit 200, with the conduit wall 205 on the outside, or outer portion of the conduit 200, and the membrane 150 on the inside, or extending transverse to the conduit axis or flow through the conduit 200. When gas flows through the conduit 200, the pressure of the gas may cause bending or flexing of the membrane 150 in the direction in which the gas is flowing.

Bending or flexing of the membrane 150 is preferably elastic, such that there is little or no loss in resiliency of the membrane 150 and that the membrane 150 returns substantially entirely back to the original shape and orientation as before the bending or flexing occurred. This enables the membrane 150 to flex and bend in both directions and to accommodate bidirectional flow through the conduit.

FIG. 2B provides another view of the flow controller conduit 200, with the membrane 150 inside the conduit wall 205. The flow controller conduit 200 may be used in conjunction with a medical ventilator and, thus, may have an inspiratory side 230 and an expiratory side 240. The use of the terms "inspiratory" and "expiratory" are used only as conventions herein, and the sides may also be referred to as a First side and a second side. Usage of "inspiratory" and "expiratory" are not intended to suggest that the present application can only be applied or used in a respiratory, or even merely only a medical, setting. Application of the present disclosure in the medical setting, or more specifically, the respiratory setting, may be indicated through other indications, such as, for example, the reference to a patient or to a ventilator. A medical ventilator may connect with the flow controller conduit 200 at connection 230 near the expiratory side 240, meaning that side is the direction of the conduit 200 that the patient would be exhaling toward.

As shown (see, e.g., FIGS. 4-6), a membrane controller 210 is positioned adjacent to the membrane 150 and in the inspiratory direction from the membrane 150. The membrane controller 210 thereby impedes bending of the membrane toward the inspiratory side 230 when air from the ventilator is directed through the conduit. Impeding bending of the membrane 150 as it bends toward the inspiratory side 230 would thereby impede gas flow within the flow controller conduit 200 in the inspiratory direction but not in the expiratory direction. Because the membrane controller 210 impedes movement of the membrane 150 in one direction but not the other, an imbalance of resistance force is created by the membranes 150, 210: in one direction the resistance to flow is greater than the resistance force in the second direction. The imbalance of resistance forces provides that a greater pressure is used to push fluid past the membrane 150 in one direction than in the other direction. This may be beneficial if, for example, a medical ventilator is used for directing air to a patient during inhalation, but the patient needs to rely on his/her own lungs for exhalation, which operates at a less pressure. Thus, more pressure may be provided from the ventilator during inhalation than during exhalation, and the membrane controller 210 permits the same conduit to be utilized for the patient by providing a valve that operates to allow air to pass through the valve at different pressures between inhalation and exhalation.

The membrane controller 210 may connect with the conduit wall 205 at only one portion of the controller 210, such that the controller 210 is able to bend when engaged by the membrane 150. The membrane controller may have any shape, for example, a symmetric shape, such as an elongate shape that resembles a line segment, an uppercase "T," a lowercase "t," or an annular shape. The membrane controller 210 may be made of a Mylar® (biaxially-oriented polyethylene terephthalate) material or other materials, such as other composites or ferrous sheet(s). The membrane controller 210 may be made of the same material as the membrane 150. Alternatively, the membrane 150 and the membrane controller 210 may be made of different materials. In some instances, it may be desirable for the membrane controller 210 to have a more streamlined shape than that of the membrane 150, such that it is less likely for the flowing fluid to press the membrane controller 210 into the membrane 150 when it should not be contacting the membrane 150

Figure 2C:
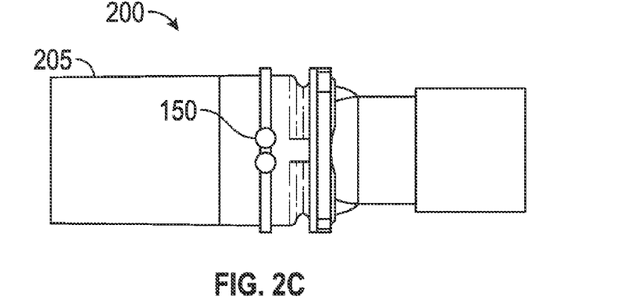
Figure 2D:
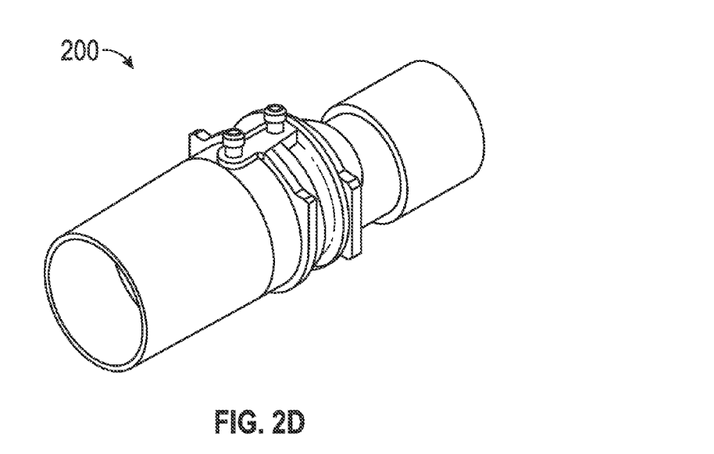

FIG. 2C provides an exterior view of the flow controller conduit 200. As shown in FIG. 2C, the membrane 150 is connected to the conduit wall 205 via the annular sheet portion 160. As a result of this connection, the membrane 150 may bend or flex in response to fluid moving through the flow controller conduit and applying a pressure to the membrane 150. FIG. 2D provides a three-dimensional exterior view of the flow controller conduit 200.

Figure 3A:
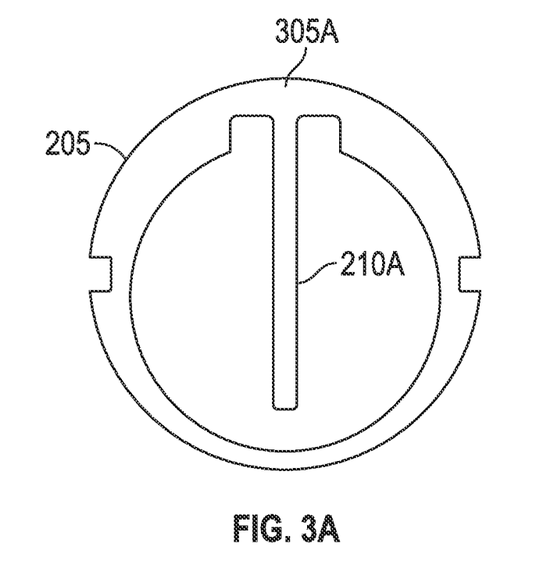
FIGS. 3A-3B illustrate examples of a membrane controller that operates in conjunction with membranes depicted in FIGS. 1A-1B.

FIGS. 3A-3B illustrates examples of a membrane controller. FIG. 3A illustrates a first example of a membrane controller 210A, which may correspond to the membrane controller 210 of FIG. 2B. As shown in FIG. 3A, the membrane controller 210 comprises a line segment, or elongate, shape that extends from a portion of the conduit wall 205 toward a portion that intersects with the conduit wall 205. In some instances, the membrane controller 210 extends substantially diametrically across the conduit 200. The membrane controller may have a width 210A of 0.050+/−0.001 inches in some instances. However, this value may vary depending upon the desired use of the membrane controller, such as, for example, operations at different pressure levels and different fluids passing through the conduit 200. As a result of the membrane controller 210A being connected to the conduit wall 205 at only one portion 305A, the membrane controller 210A may impede, but not prevent, bending of the membrane 150 in the direction from the membrane 150 toward the membrane controller 210/210A. A higher pressure will be required for the membrane to bend or flex when fluid is moving in the direction from the membrane 150 to the membrane controller 210/210A than when fluid is moving in the other direction.

Figure 3B:
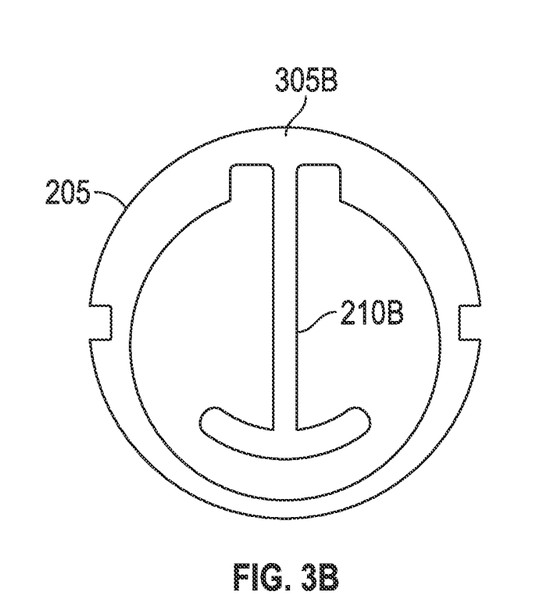

FIG. 3B illustrates further examples of a membrane controller 210B, which may correspond to the membrane controller 210 of FIG. 2B. As shown in FIG. 3B, the membrane controller comprises a portion that extends transversely to a long axis of the elongate, or line, segment. For example, as depicted in FIG. 3B, the membrane controller can comprise an uppercase "T" shape that extends from the conduit wall 205 and intersects with the conduit wall 205 at only one portion 305B, which is where the controller is coupled to the conduit wall at the base or bottom of the uppercase "T" shape. In some embodiments, the membrane controller 210B may be symmetric relative a diameter of the conduit wall passing through the intersection point 305B.

The membrane controller 210B may be a desirable configuration in some instances, for example, there may be applications and pressure ranges that create a resonance frequency in the bending or flexing of the membrane 150. In such instances, the membrane 150 may be inclined to twist about an axis or fluctuate back and force quickly, thereby creating a constantly changing pressure differential and flow rate across the membrane. By including a transversely extending portion toward a moving end of the membrane controller 210, it is possible to provide a greater resistance to twisting of the membrane 150 and a greater mass at the opening portion of the membrane 150, which can reduce the likelihood or severity of resonant frequencies during operation.

Additional designs for the membrane controller 210, different from those of the membrane controllers 210A and 210B are possible. For example, the membrane controller 210 may have a lowercase "t" shape that intersects with the conduit wall 205 at one segment at the top or the bottom of the lowercase "t" shape. In another example, the membrane controller 210 may have an annular shape. In the annular shape example, the outer diameter of the membrane controller 210 is smaller than the inner diameter of the conduit wall 205 and smaller than an outer diameter of the membrane 150.

Figure 4:
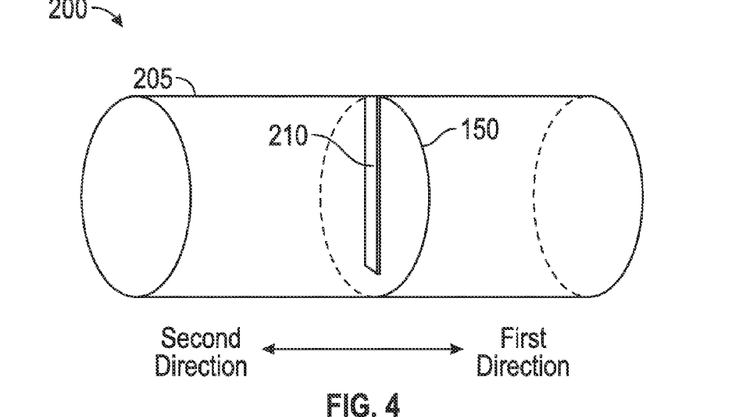
FIG. 4 illustrates an examples of a flow controller conduit including a membrane and a membrane controller.

FIG. 4 illustrates an example of a flow controller conduit 200 including a membrane 150 and a membrane controller 210. The membrane 150 and the membrane controller 210 may be aligned with the conduit wall 205 by, for example, notches along the perimeter of the annular portion or by, for example, apertures through the annular portion that permit only, one orientation when assembled. The membrane 150 is preferably positioned adjacent to the membrane controller 210 and in a first direction (i.e., on one side) from the membrane controller 210. Gas may flow through the flow controller conduit 200, via the membrane 150, in either the first direction or a second direction. The second direction may be opposite the first direction. When gas flows through the flow controller conduit 200 in the first direction, the gas has to provide at least a first pressure to cause the membrane 150 to bend or flap. However, the membrane controller 210 need not be disturbed or contacted by the membrane 150. When gas flows through the flow controller conduit 210 in the second direction, the gas has to provide at least a second pressure to cause both the membrane 150 and the membrane controller 210 to bend or flap. The second pressure is greater than the first pressure.

Figure 5:
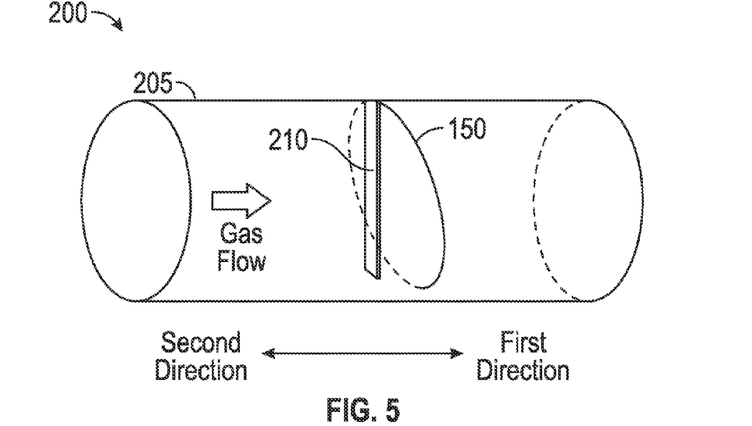
FIG. 5 illustrates an example of a flow controller conduit including a membrane and a membrane controller, where the membrane is deflected away from the membrane controller.

FIG. 5 illustrates examples of a flow controller conduit 200 including a membrane 150 and a membrane controller 210, where the membrane 150 is deflected or bends away from the membrane controller 210. As shown in FIG. 5, the flow controller conduit 200 has gas flow in a first direction from the membrane controller 210 to the membrane 150. As a result, the membrane 150 is deflected or bends under the pressure from the gas flow, and the membrane controller 210 remains substantially in the rest position. In some embodiments, the membrane 150 is deflected or bends upon the gas applying a first, low level of pressure, yet at that first, low level of pressure, the membrane controller 210 does not substantially deflect or bend (i.e., the membrane controller 210 does not contact the membrane 150).

Figure 6:
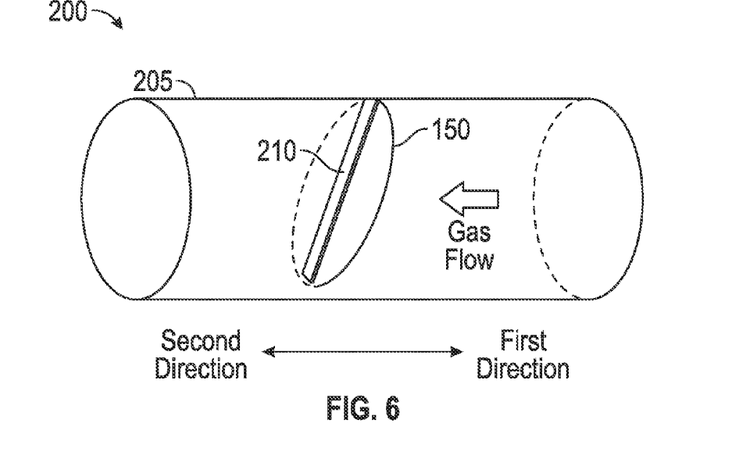
FIG. 6 illustrates an example of a flow controller conduit including a membrane and a membrane controller, where the membrane is deflected toward and engages the membrane controller.

FIG. 6 illustrates examples of a flow controller conduit 200 including a membrane 150 and a membrane controller 210, where the membrane 150 is deflected or bends toward and engages the membrane controller 210. As shown in FIG. 6, the flow controller conduit 200 has gas flow in a second direction from the membrane 150 toward the membrane controller 210. As a result, the membrane 150 is deflected or bends toward and engages the membrane controller 210, causing the membrane 150 to contact the membrane controller 210 and to result in deflection of the membrane controller 210. In some embodiments, the membrane 150 deflects or bends both the membrane 150 and the membrane controller 210 upon the gas applying a second, high level of pressure. In FIGS. 5-6, as in FIG. 4, the membrane 150 and the membrane controller 210 may be coupled to the conduit wall 205 and bends at or adjacent to a connecting portion with the conduit wall 205.

Some implementations of the subject technology are described above. However, alternative implementations are possible. For instance, the subject technology is described above in conjunction with a gas flowing through a flow controller conduit. However, it should be noted that the subject technology may be implemented with a liquid in place of the gas. Furthermore, while implementations of the subject technology is described in many portions herein as being implemented in conjunction with a medical ventilator, the subject technology is not limited to the medical ventilation fields, or even generically to medical fields. For example, the subject technology may be used in a bidirectional oil conduit, where oil or gas fuel is moved in one direction at a high pressure and in another direction at a low pressure.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item: rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims. If any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112 (f) unless the element is expressly recited using the phrase "module for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

What is claimed is:

1. A flow controller conduit comprising:
   a conduit comprising a conduit wall;
   a membrane coupled to the conduit wall, the membrane obstructing gas flow through the conduit when the membrane is in a closed position; and
   a membrane controller coupled to the conduit wall adjacent the membrane, the membrane, in the closed position, being spaced apart in a first direction from the membrane controller;
   wherein the membrane bends in the first direction to permit a gas flow through the conduit in the first direction, and the membrane bends in a second direction, different from the first direction, to contact and deflect the membrane controller, the membrane controller impeding the bending of the membrane to restrict a gas flow through the conduit and membrane in the second direction.

2. The flow controller conduit of claim 1, wherein the second direction is opposite the first direction, and wherein the conduit wall extends in the first direction and the second direction.

3. The flow controller conduit of claim 2, wherein the membrane, when in the closed position, resides within a plane perpendicular to the first direction and the second direction.

4. The flow controller conduit of claim 2, wherein the membrane controller, when in a rest position, resides within a plane perpendicular to the first direction and the second direction.

5. The flow controller conduit of claim 1, wherein the membrane controller comprises an elongate shape having a transverse portion that extends in a direction transverse to the elongate shape.

6. The flow controller conduit of claim 1, wherein the membrane controller further comprises an annular membrane conduit wall connection.

7. The flow controller conduit of claim 1, wherein the membrane comprises a circular shape that is coupled to the conduit wall at only one segment of the circular shape.

8. The flow controller conduit of claim 1, wherein the membrane controller comprises a biaxially-oriented polyethylene terephthalate material.

9. The flow controller conduit of claim 8, wherein the membrane comprises a biaxially-oriented polyethylene terephthalate material and comprises a substantially equal thickness to the membrane controller.

10. The flow controller conduit of claim 8, wherein the membrane controller comprises a thickness that is greater than a thickness of the membrane.

11. The flow controller conduit of claim 1, wherein the membrane controller contacts the membrane only when the membrane bends toward the membrane controller.

12. A membrane controller comprising:
    an annular portion configured to contact a conduit wall, such that the membrane controller is configured to be secured within a conduit by the contact between the annular portion and the conduit wall; and
    an elongate portion extending across a central opening of the annular portion, the elongate portion comprising a first end portion connected to the annular portion, and a second end portion separated from the annular portion by a first slit, wherein second and third slits intersect the first slit at the first end portion; and
    wherein the membrane controller is configured (i) to be positioned within the conduit and spaced apart on one side of a flexible membrane and (ii) to deflect when contacted by the flexible membrane against the elongate portion when the flexible membrane is bended toward the membrane controller.

13. The membrane controller of claim 12, wherein the elongate portion is configured not to contact the flexible membrane when the flexible membrane is deflected away from the membrane controller.

14. The membrane controller of claim 12, wherein the elongate portion comprises a biaxially-oriented polyethylene terephthalate material.

15. The membrane controller of claim 12, wherein the elongate portion comprises a transverse segment, spaced from the first end portion of the elongate portion, that extends transversely to a long axis of the elongate portion.

16. The membrane controller of claim 12, wherein the elongate portion extends substantially diametrically across the central opening of the annular portion.

17. A method of controlling flow through a conduit, the method comprising:
   providing a membrane controller comprising:
      an elongate portion; and
      an annular portion secured within the conduit and positioned within the conduit and spaced apart on one side of a flexible membrane, such that the membrane controller is contacted by the flexible membrane against the elongate portion when the flexible membrane is deflected toward the membrane controller;
   the elongate portion extending across a central opening of the annular portion, and the elongate portion being connected to the annular portion at only one end of the elongate portion; and
   impeding a fluid flow conducted through the conduit in a first direction, wherein the fluid flow in the first direction causes the flexible membrane to bend toward and deflect the membrane controller; and
   permitting a fluid flow through the conduit in a second direction, wherein the fluid flow in the second direction causes the flexible membrane to bend away from the membrane controller.

18. The method of claim 17, wherein any of the impeding and permitting a fluid flow conducted through the conduit comprises connecting the conduit between a ventilator and a patient.

19. The method of claim 17, wherein the membrane controller and the flexible membrane comprise biaxially-oriented polyethylene terephthalate material.

20. The flow controller conduit of claim 1, wherein the membrane controller comprises an elongate shape, extends diametrically across the conduit, and contacts the conduit wall at a first end of the elongate shape, but not at a second end of the elongate shape.

\* \* \* \* \*